United States Patent
Craggs et al.

(10) Patent No.: US 9,476,088 B2
(45) Date of Patent: Oct. 25, 2016

(54) ANALYTE MEASUREMENT METHOD AND SYSTEM WITH HEMATOCRIT COMPENSATION

(75) Inventors: Adam Craggs, Inverness (GB); Michael Malecha, Muir of Ord (GB); Steve Blythe, Inverness (GB)

(73) Assignee: LifeScan Scotland Limited, Inverness (GB)

(*) Notice: Subject to any disclaimer, the term of this patent is extended or adjusted under 35 U.S.C. 154(b) by 789 days.

(21) Appl. No.: 13/812,122

(22) PCT Filed: Sep. 13, 2011

(86) PCT No.: PCT/GB2011/001342
§ 371 (c)(1),
(2), (4) Date: Apr. 26, 2013

(87) PCT Pub. No.: WO2012/035297
PCT Pub. Date: Mar. 22, 2012

(65) Prior Publication Data
US 2013/0199943 A1    Aug. 8, 2013

Related U.S. Application Data

(60) Provisional application No. 61/382,234, filed on Sep. 13, 2010.

(51) Int. Cl.
G01N 27/327    (2006.01)
C12Q 1/54      (2006.01)
A61B 5/1486    (2006.01)

(52) U.S. Cl.
CPC .............. *C12Q 1/54* (2013.01); *A61B 5/1486* (2013.01); *G01N 27/3273* (2013.01)

(58) Field of Classification Search
None
See application file for complete search history.

(56) References Cited

U.S. PATENT DOCUMENTS

6,241,862 B1   6/2001  McAleer et al.
6,340,428 B1   1/2002  Ikeda et al.
(Continued)

FOREIGN PATENT DOCUMENTS

CN   1938590 A    3/2007
CN   102918388 A  2/2013
(Continued)

OTHER PUBLICATIONS

Notice of Reasons for Rejection issued in related Japanese Patent Application No. 2013-528759, transmitted on Jun. 30, 2015, 5 pages.
(Continued)

*Primary Examiner* — J. Christopher Ball

(57) ABSTRACT

Described and illustrated herein are systems and exemplary methods of operating an analyte measurement system having a meter and a test strip. In one embodiment, the method may be achieved by applying a first test voltage between a reference electrode and a second working electrode and applying a second test voltage between the reference electrode and a first working electrode; measuring a first test current, a second test current, a third test current and a fourth test current at the second working electrode after a blood sample containing an analyte is applied to the test strip; measuring a fifth test current at the first working electrode; estimating a hematocrit-corrected analyte concentration from the first, second, third, fourth and fifth test currents; and annunciating the hematocrit-corrected analyte concentration.

14 Claims, 9 Drawing Sheets

(56) References Cited

U.S. PATENT DOCUMENTS

| | | |
|---|---|---|
| 2005/0109618 A1 | 5/2005 | Davies |
| 2007/0138026 A1 | 6/2007 | Fujiwara et al. |
| 2007/0227912 A1 | 10/2007 | Chatelier et al. |
| 2009/0184004 A1 | 7/2009 | Chatelier et al. |
| 2009/0194432 A1 | 8/2009 | Deng |
| 2013/0095510 A1 | 4/2013 | Malecha et al. |

FOREIGN PATENT DOCUMENTS

| | | | |
|---|---|---|---|
| EP | 1742045 | A1 | 1/2007 |
| JP | H11344462 | A | 12/1999 |
| JP | 2007514929 | A | 6/2007 |
| JP | 2007271622 | A | 10/2007 |
| JP | 2009168815 | A | 7/2009 |
| WO | 2008040990 | A2 | 4/2008 |
| WO | 2008040998 | A2 | 4/2008 |
| WO | 2009015316 | A1 | 1/2009 |
| WO | 2011121292 | A1 | 10/2011 |

OTHER PUBLICATIONS

Patent Examination Report No. 1 issued in related Australian Patent Application No. 2011303639, issued Feb. 14, 2014, 3 pages.

First Office Action issued in related Chinese Patent Application No. 201180043986.5, issued Jul. 7, 2014, 24 pages.

Search Report issued in related Chinese Patent Application No. 201180043986.5, dated May 27, 2014, 2 pages.

International Search Report and Written Opinion issued in related International Application No. PCT/GB2011/001342, mailed Dec. 22, 2011, 11 pages.

ANALYTE MEASUREMENT METHOD AND SYSTEM WITH HEMATOCRIT COMPENSATION

This application claims the benefits of priority under the Paris Convention, 35 USC §§119, 120, or 365 to U.S. Provisional Patent Application 61/382,234, filed on Sep. 13, 2010, titled "ANALYTE MEASUREMENT METHOD AND SYSTEM WITH HEMATOCRIT COMPENSATION" which application is incorporated by reference in its entirety herein.

BACKGROUND

Electrochemical sensors have been used to detect or measure the presence of substances in fluid samples. Electrochemical sensors include a reagent mixture containing at least an electron transfer agent (also referred to as an "electron mediator") and an analyte specific bio-catalytic protein (e.g. a particular enzyme), and one or more electrodes. Such sensors rely on electron transfer between the electron mediator and the electrode surfaces and function by measuring electrochemical redox reactions. When used in an electrochemical biosensor system or device, the electron transfer reactions are monitored via an electrical signal that correlates to the concentration of the analyte being measured in the fluid sample.

The use of such electrochemical sensors to detect analytes in bodily fluids, such as blood or blood derived products, tears, urine, and saliva, has become important, and in some cases, vital to maintain the health of certain individuals. In the health care field, people such as diabetics, for example, must monitor a particular constituent within their bodily fluids. A number of systems are capable of testing a body fluid, such as, blood, urine, or saliva, to conveniently monitor the level of a particular fluid constituent, such as, cholesterol, proteins, and glucose. Patients suffering from diabetes, a disorder of the pancreas where insufficient insulin production prevents the proper digestion of sugar, have a need to carefully monitor their blood glucose levels on a daily basis. Routine testing and controlling blood glucose for people with diabetes can reduce their risk of serious damage to the eyes, nerves, and kidneys.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration) is observed at low hematocrit. At high hematocrit, for example, the red blood cells may impede the reaction of enzymes and electrochemical mediators, reduce the rate of chemistry dissolution since there less plasma volume to solvate the chemical reactants, and slow diffusion of the mediator. These factors can result in a lower than expected glucose reading as less current is produced during the electrochemical process. Conversely, at low hematocrit, fewer red blood cells may affect the electrochemical reaction than expected, and a higher measured current can result. In addition, the blood sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cell and attenuate the affect of low hematocrit on concentration determinations. Other test strips have included lysis agents and systems configured to determine hemoglobin concentration in an attempt to correct hematocrit. Further, biosensors have been configured to measure hematocrit by measuring optical variations after irradiating the blood sample with light, or measuring hematocrit based on a function of sample chamber fill time. These sensors have certain disadvantages.

SUMMARY OF THE DISCLOSURE

Applicants have recognized a need for a system and method that can be used to determine an accurate glucose concentration that avoids the disadvantages in the field.

In view of the foregoing and in accordance with one aspect, there is provided a method of operating an analyte measurement system having a meter and a test strip. The test strip may include a reference electrode, a first working electrode and a second working electrode in which the first electrodes are coated with a reagent layer. The meter may include an electronic circuit for applying a test voltage between the reference electrode and the first working electrode and for applying a second test voltage between the reference electrode and the second working electrode. The meter also may include a signal processor for measuring a plurality of test currents and for calculating a glucose concentration from the test currents. The method may be achieved by applying, with the test circuit, a first test voltage between a reference electrode and a second working electrode coated with a reagent layer having a mediator disposed thereon of the test strip and applying a second test voltage between the reference electrode and a first working electrode coated with a reagent layer having a mediator disposed thereon; measuring a first test current, a second test current, a third test current and a fourth test current at the second working electrode after a blood sample is applied to the test strip to cause a transformation of glucose in the blood from one form of glucose enzyme into another form of glucose enzyme and generate a current by an electrochemical re-oxidation of a reduced mediator; measuring a fifth test current at the first working electrode; determining, with the microprocessor, a glucose concentration based on the first, second, third, fourth and fifth test currents; and annunciating the glucose concentration.

In yet another aspect, there is provided a method of operating an analyte measurement system having a meter and a test strip. The test strip may include a reference electrode, a first working electrode and a second working electrode in which the first electrodes are coated with a reagent layer. The meter may include an electronic circuit for applying a test voltage between the reference electrode and the first working electrode and for applying a second test voltage between the reference electrode and the second working electrode. The meter also may include a signal processor for measuring a plurality of test currents and for calculating a glucose concentration from the test currents. The method may be achieved by applying a first test voltage between a reference electrode and a second working electrode coated with a reagent layer and applying a second test voltage between a reference electrode and a first working electrode coated with a reagent layer; measuring a first test current, a second test current, a third test current and a fourth test current at the second working electrode after a blood sample containing glucose is applied to the test strip to cause a transformation of glucose in the blood from one form of glucose enzyme into another form of glucose enzyme and generate a current by an electrochemical re-oxidation of a reduced mediator; measuring a fifth test current at the first working electrode; determining the glucose concentration from the first, second, third, fourth and fifth test currents with an equation of the form:

$$G = \frac{\left(\frac{a*I_5 + b}{\left(\frac{c*\left(\frac{I_2 - I_1}{d}\right) + e}{f*(I_2*I_1) + g}\right) * \left(\frac{h*\left(\frac{I_4 - I_3}{k}\right) + p}{q*(I_4*I_3) + s}\right)}\right) - \text{intercept}}{\text{slope}}$$

where:
G comprises the glucose concentration;
$I_1$ comprises the first test current;
$I_2$ comprises the second test current;
$I_3$ comprises the third test current;
$I_4$ comprises the fourth test current;
$I_5$ comprises the fifth test current;
a, b, c, d, e, f, g, h, k, p, q and s each comprises empirically derived constants;
intercept comprises an intercept value determined from a linear regression of a plot of $$\frac{a*I_5 + b}{\left(\frac{c*\left(\frac{I_2 - I_1}{d}\right) + e}{f*(I_2*I_1) + g}\right) * \left(\frac{h*\left(\frac{I_4 - I_3}{k}\right) + p}{q*(I_4*I_3) + s}\right)}$$

versus a reference glucose concentration; and
slope comprises a slope value determined from a linear regression of a plot of $$\frac{a*I_5 + b}{\left(\frac{c*\left(\frac{I_2 - I_1}{d}\right) + e}{f*(I_2*I_1) + g}\right) * \left(\frac{h*\left(\frac{I_4 - I_3}{k}\right) + p}{q*(I_4*I_3) + s}\right)}$$

versus the reference glucose concentration.

In a further embodiment, there is provided a method of operating an analyte measurement system having a meter and a test strip. The test strip may include a reference electrode, a first working electrode and a second working electrode in which the first electrodes are coated with a reagent layer. The meter may include an electronic circuit for applying a test voltage between the reference electrode and the first working electrode and for applying a second test voltage between the reference electrode and the second working electrode. The meter also may include a signal processor for measuring a plurality of test currents and for calculating a glucose concentration from the test currents. The method may be achieved by: applying a first test voltage between a reference electrode and a second working electrode coated with a reagent layer and applying a second test voltage between a reference electrode and a first working electrode coated with a reagent layer; measuring a first test current, a second test current, a third test current and a fourth test current at the second working electrode after a blood sample containing glucose is applied to the test strip to cause a transformation of glucose in the blood from one form of glucose enzyme into another form of glucose enzyme and generate a current by an electrochemical re-oxidation of a reduced mediator; measuring a fifth test current at the first working electrode; and determining the hematocrit-corrected test current by determining a ratio of a third corrected current to a first corrected current multiplied by a second corrected current.

In a further embodiment, an analyte measurement system to measure a glucose concentration in physiological fluid of a user is provided. The system includes a test strip and an analyte meter. The test strip includes a substrate having a reference electrode, a first working electrode and a second working electrode coated with a reagent layer having a mediator disposed thereon. The electrodes are connected to corresponding contact pads. The analyte meter includes a microprocessor and a test circuit in connection with a test strip port that receives the contact pads of the test strip so that the meter is configured to apply a test voltage after deposition of physiological fluid on the electrodes to induce an electrochemical transformation of the physiological fluid proximate the electrodes and determine a hematocrit-corrected glucose concentration of the physiological fluid from measured first, second, third, fourth and fifth test currents at first, second, third, fourth and fifth discrete intervals after application of the test voltage by the meter.

In yet a further embodiment, an analyte measurement system to measure a glucose concentration in physiological fluid of a user is provided. The system includes a test strip and an analyte meter. The test strip includes a substrate having a reference electrode, a first working electrode and a second working electrode coated with a reagent layer having a mediator disposed thereon. The electrodes are connected to corresponding contact pads. The analyte meter includes a microprocessor and a test circuit in connection with a test strip port that receives the contact pads of the test strip so that the meter is configured to apply a test voltage after deposition of physiological fluid on the electrodes and determine a hematocrit-corrected glucose concentration from measured first, second, third, fourth and fifth test currents so that at least 98% of plural samples are within an ISO (International Standards Organization) bias criteria of about ±15%, with at least 95% of the plural samples are within ISO bias criteria of about ±12%, and at least 88% of the samples are within ISO bias criteria of about ±10%.

These and other embodiments, features and advantages of the invention will become apparent to those skilled in the art when taken with reference to the following more detailed description of the exemplary embodiments in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (in which like numerals represent like elements), of which.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1A:
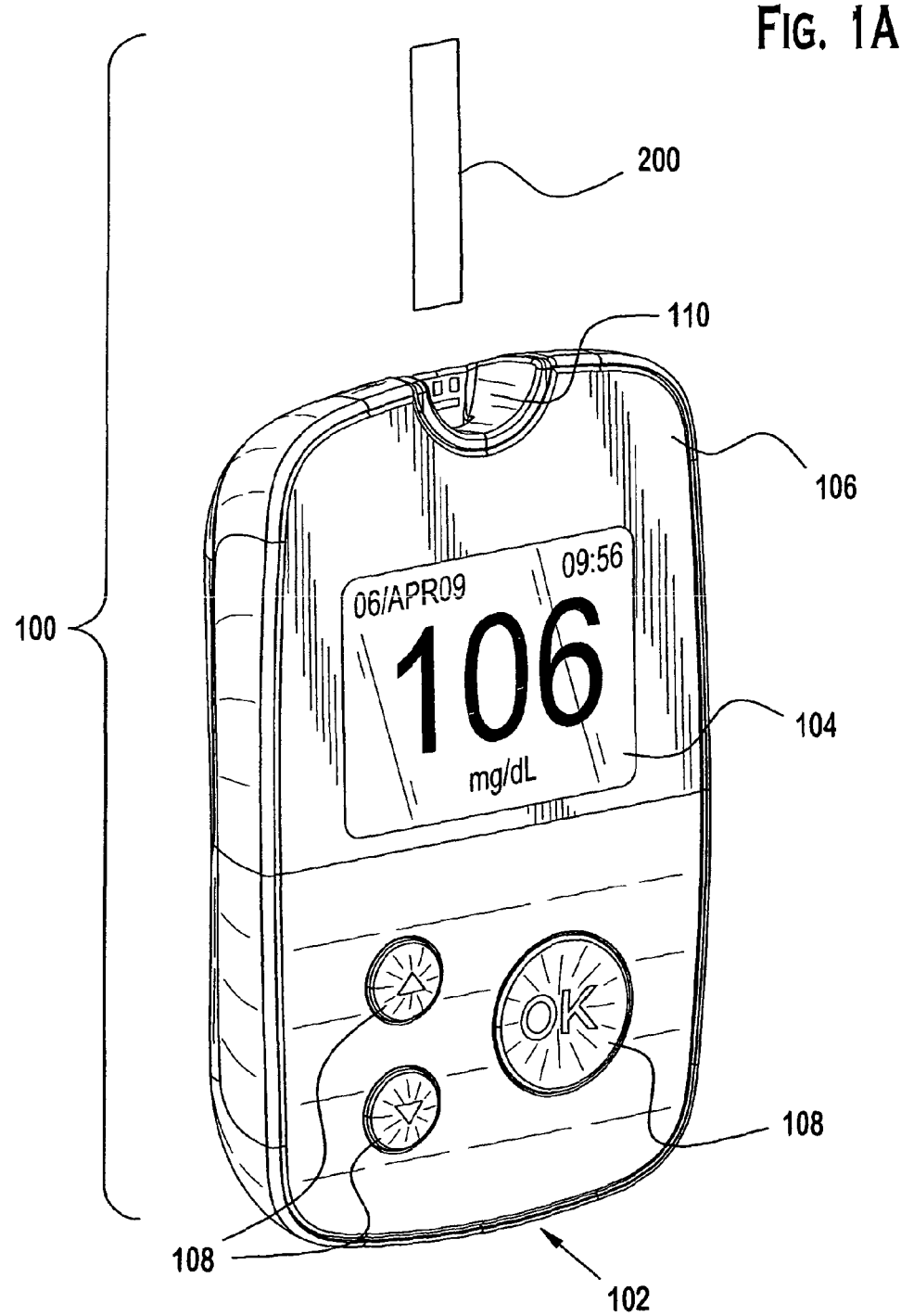
FIG. 1A illustrates an exemplary embodiment of a top view of a system for measuring an analyte concentration.

FIG. 1A illustrates a system 100 for measuring an analyte concentration in which system 100 may include a meter 102 and a test strip 200. Meter 102 may include a display 104, a housing 106, a plurality of user interface buttons 108, and a strip port 110. Meter 102 further may include electronic circuitry within housing 106 as further described in relation to FIG. 1B. A proximal portion of test strip 200 may be inserted into strip port 110. Display 104 may annunciate an analyte concentration, e.g., glucose concentration, and may be used to show a user interface for prompting a user on how to perform a test. As used here, the term "annunciate" and variations on the root term indicate that an announcement may be provided via text, audio, visual or a combination of all modes of communication to a user, a caretaker of the user, or a healthcare provider. The plurality of user interface buttons 108 allow a user to operate meter 102 by navigating through the user interface software. Display 104 may optionally include a backlight.

Figure 1B:
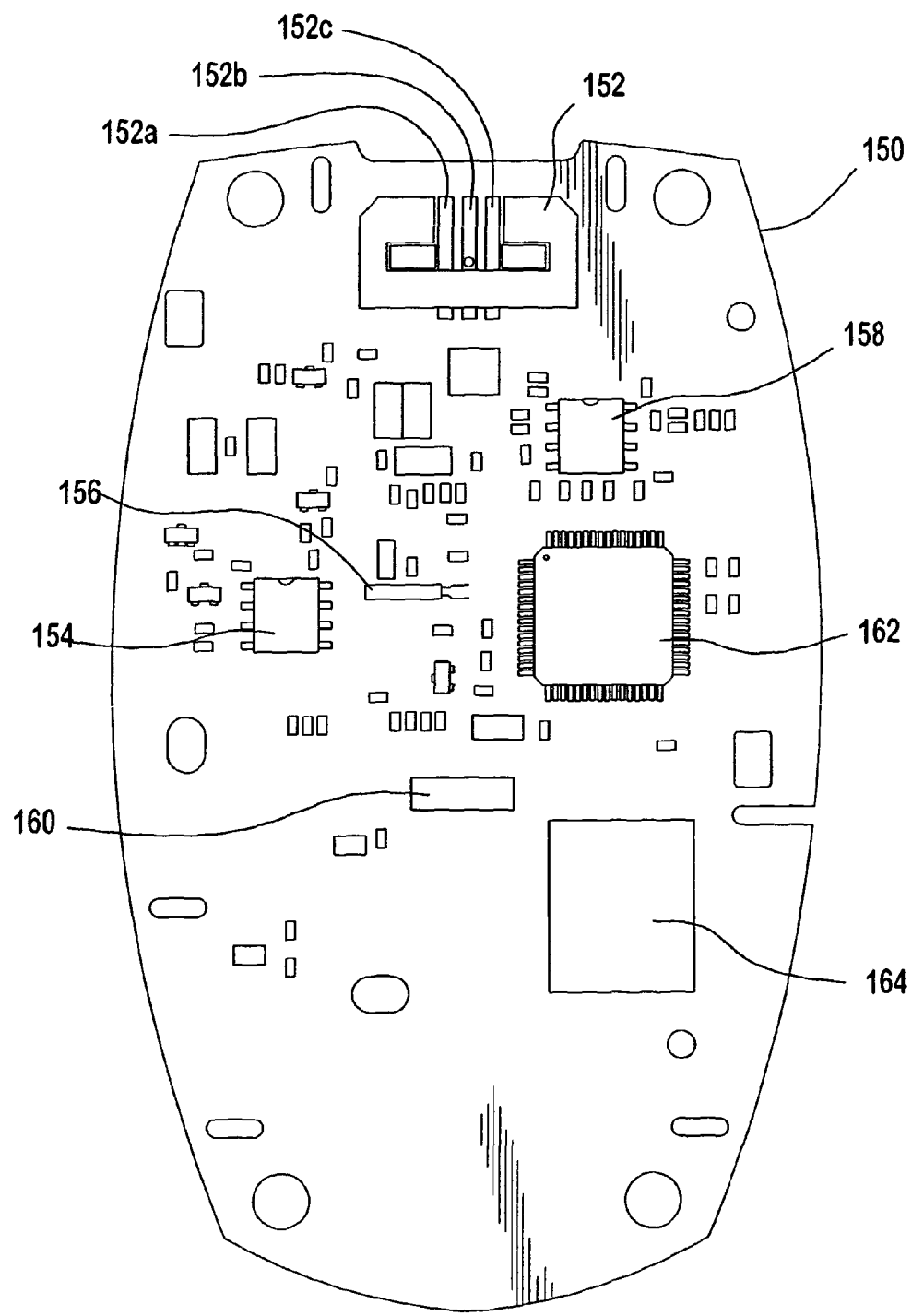
FIG. 1B illustrates an exemplary circuit board of the electrical components disposed in the analyte measurement device of FIG. 1A.

Disposed inside housing 106 includes, as shown in FIG. 1B, a circuit board 150 with a microcontroller 162 coupled to a memory 154, clock 156, operational amplifier 158, and display connector 160. The op-amp 158 and microcontroller 162 are operatively connected to a strip port connector 152 with contacts 152a, 152b, and 152b for mechanical contact with corresponding conductive tracks on the test strip 200. To facilitate communication with other data management devices, a wireless transceiver module 164 is provided to allow for bi-directional communication of data stored in the memory 154 of the unit 100. On the other side of circuit board 150 a power source in the form of a battery (not shown) is provided. A data port may also be provided. It should be noted that the meter unit 100 is preferably sized and configured to be handheld and the transceiver 164 can be for use with either or both of a short-range wireless network (e.g., Bluetooth or Wi-Fi and the like) or a longer range wireless network (e.g., GSM, CDMA, 3G and the like).

Microcontroller 162 can be electrically connected to strip port 152, operational amplifier circuit 158, first wireless module 164, display 104, non-volatile memory 154, clock 156, data port, and user interface buttons 108. Data entered via the buttons, transceiver or glucose measurement circuit can include values representative of analyte concentration, or in the context of the analyte concentration values coupled with information, which are related to the everyday lifestyle of an individual. Information, which is related to the everyday lifestyle, can include food intake, medication use, occurrence of health check-ups, and general health condition and exercise levels of an individual coupled to or "tagged" with the analyte concentration value of the user at specific time of the day or week.

Operational amplifier circuit 158 can be two or more operational amplifiers configured to provide a portion of the potentiostat function and the current measurement function. The potentiostat function can refer to the application of a test voltage between at least two electrodes of a test strip. The current function can refer to the measurement of a test current resulting from the applied test voltage to the test strip 200. The current measurement may be performed with a current-to-voltage converter. Microcontroller 162 can be in the form of a mixed signal microprocessor (MSP) such as, for example, the Texas Instrument MSP430F2419. The TI-MSP430F2419 can be configured to also perform a portion of the potentiostat function and the current measurement function. In addition, the MSP430F2419 can also include volatile and non-volatile memory. In another embodiment, many of the electronic components can be integrated with the microcontroller in the form of an application specific integrated circuit (ASIC).

Strip port 152 can be configured to form an electrical connection to the test strip 200. Display connector 160 can be configured to attach to display 104. Display 104 can be in the form of a liquid crystal display for reporting measured glucose levels, and for facilitating entry of lifestyle related information and for manipulation of graphical data, pictorial results and motion video. Display 104 may also include a backlight. Data port can accept a suitable connector attached to a connecting lead, thereby allowing meter unit 100 to be linked to an external device such as a personal computer. Data port can be any port that allows for transmission of data such as, for example, a serial, USB, or a parallel port. Clock 156 can be configured for measuring time and be in the form of an oscillating crystal.

Figure 2:
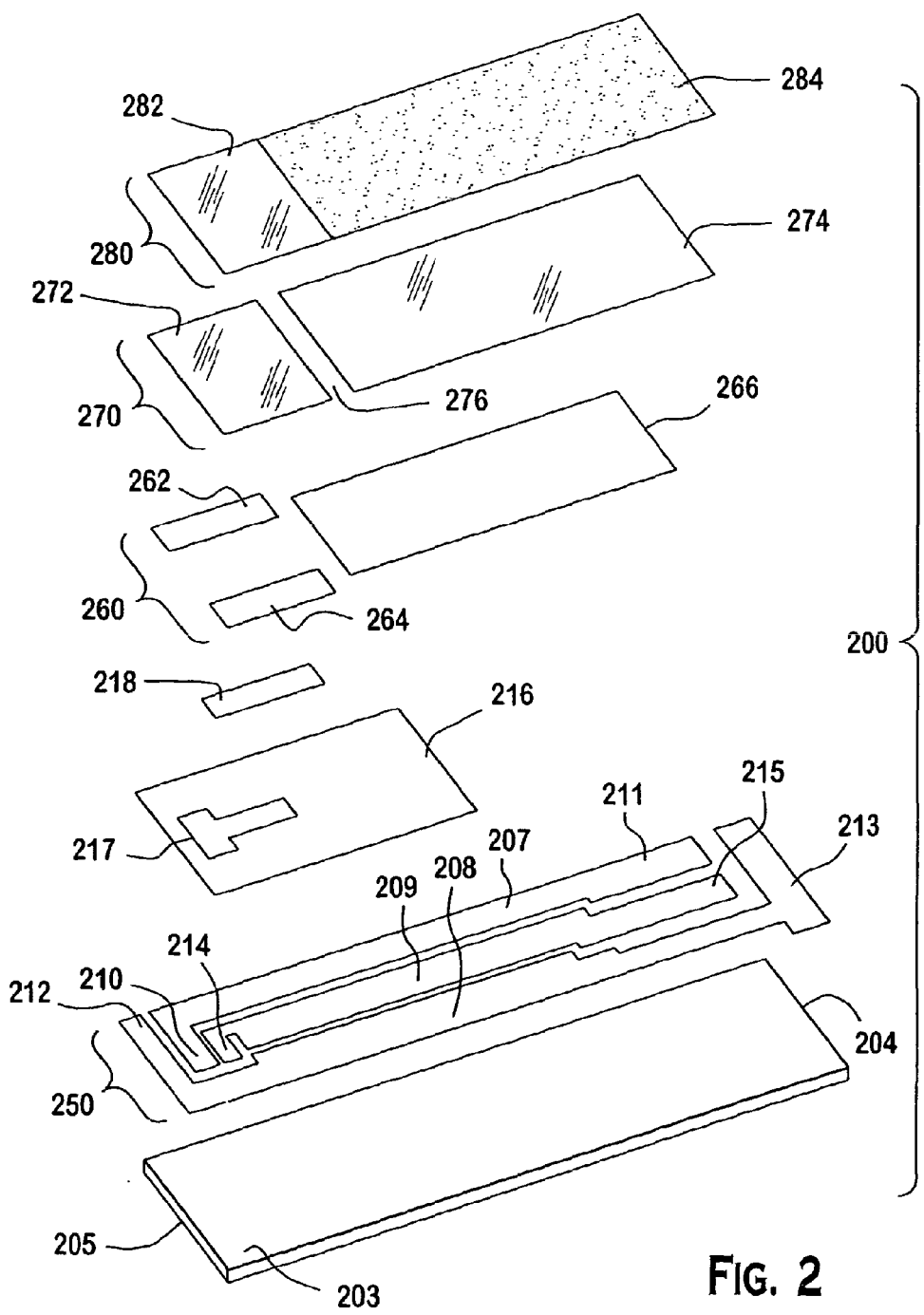
FIG. 2 illustrates an exemplary embodiment of a perspective exploded view of a test strip.
Figure 3:
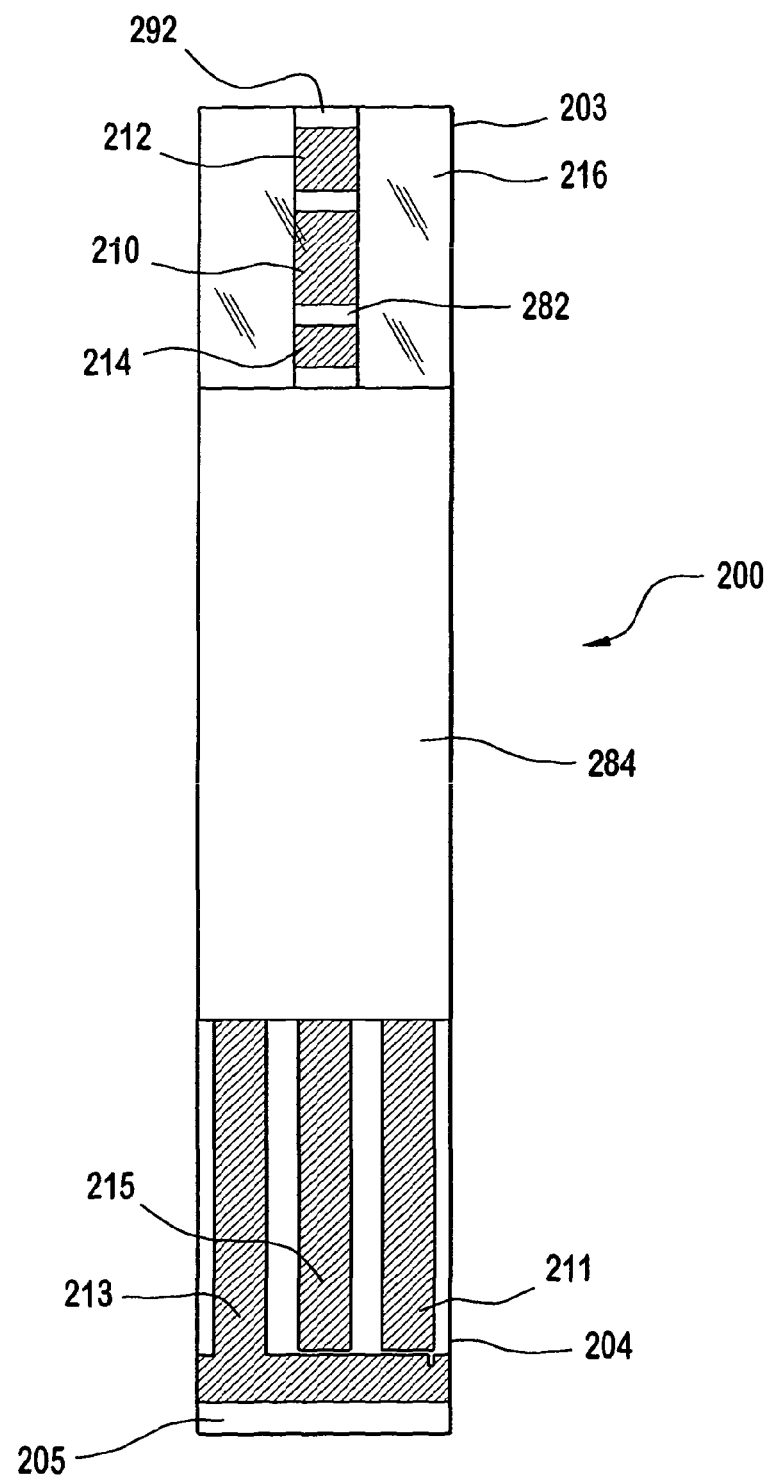
FIG. 3 illustrates an exemplary embodiment of a top view of the test strip shown in FIG. 2.

FIGS. 2 and 3 are exemplary exploded perspective and top assembled views, respectively, of test strip 200, which may include seven layers disposed on a substrate 205. The seven layers disposed on substrate 205 may be a conductive layer 250, an insulation layer 216, a reagent layer 218, an adhesive layer 260, a hydrophilic layer 270, and a top layer 280. Test strip 200 may be manufactured in a series of steps where the conductive layer 250, insulation layer 216, reagent layer 218, and adhesive layer 260 are sequentially deposited on substrate 205 using, for example, a screen-printing process. Hydrophilic layer 270 and top layer 280 may be disposed from a roll stock and laminated onto substrate 205 as either an integrated laminate or as separate layers. Test strip 200 has a distal portion 203 and a proximal portion 204, as shown in FIG. 2.

Test strip 200 may include a sample-receiving chamber 292 through which a blood sample may be drawn. Sample-receiving chamber 292 may include an inlet at a proximal end of test strip 200. An outlet or air vent is included in hydrophilic layer 270, as will be described below. A blood sample may be applied to the inlet to fill a sample-receiving chamber 292 so that an analyte concentration may be measured. The side edges of a cut-out portion of adhesive layer 260 located adjacent to reagent layer 218 defines a wall of sample-receiving chamber 292, as illustrated in FIG. 2. A bottom portion or "floor" of sample-receiving chamber 292 may include a portion of substrate 205, conductive layer 250, and insulation layer 216. A top portion or "roof" of sample-receiving chamber 292 may include distal hydrophilic portion 282.

For test strip 200, as illustrated in FIG. 2, substrate 205 may be used as a foundation for helping support subsequently applied layers. Substrate 205 may be in the form of a polyester sheet such as a polyethylene tetraphthalate (PET) material. Substrate 205 may be in a roll format, nominally 350 microns thick by 370 millimeters wide and approximately 60 meters in length.

A conductive layer 250 is required for forming electrodes that may be used for the electrochemical measurement of glucose. Conductive layer 250 may be made from a carbon ink that is screen-printed onto substrate 205. In a screen-printing process, carbon ink is loaded onto a screen and then transferred through the screen using a squeegee. The printed carbon ink may be dried using hot air at about 140° C. The carbon ink may include VAGH resin, carbon black, graphite, and one or more solvents for the resin, carbon and graphite mixture. More particularly, the carbon ink may incorporate a suitable ratio of carbon black:VAGH resin in the carbon ink.

For test strip 200, conductive layer 250 may include a reference electrode 210, a first working electrode 212, a second working electrode 214, a reference contact pad 211, a first contact pad 213, a second contact pad 215, a reference electrode track 207, a first working electrode track 208 and a second working electrode track 209. In the embodiment shown in FIG. 2, reference electrode 210 is located in between first working electrode 212 and second electrode 214 such that cross-talk between first and second working electrodes 212 and 214 is minimized.

Conductive layer 250 may be formed from a carbon ink. Reference contact pad 211, first contact pad 213 and second contact pad 215 may be configured to electrically connect to a test meter. Reference electrode track 207 provides an electrically continuous pathway from reference electrode 210 to reference contact pad 211. Similarly, first working electrode track 208 provides an electrically continuous pathway from first working electrode 12 to first contact pad 213. Similarly, second working electrode track 209 provides an electrically continuous pathway from second working electrode 214 to second contact pad 215.

Insulation layer 216 may include an aperture 217 that exposes a portion of reference electrode 210, first working electrode 212, and second working electrode 214, which may be wetted by a liquid sample. The area of first working electrode 212, second working electrode 214, and reference electrode 210 may be defined as the area exposed to the liquid sample. In addition to defining an electrode area, insulation layer 216 prevents a liquid sample from touching the electrode tracks 207, 208, and 209. It is believed that the functional area of a working electrode should be accurately defined because the magnitude of the test current is directly proportional to the effective area of the electrode. As an example, insulation layer 216 may be Ercon E6110-116 Jet Black Insulayer™ ink that may be purchased from Ercon, Inc. The test strip at this point may be treated with plasma. The plasma is created by high voltage AC at atmospheric temperatures and pressures. The resulting plasma, consisting of ionised, highly energetic particles is swept downstream in an air current to impact the substrate. Plasma treatment is used to modify the surface of the screen-printed carbon based electrodes. This surface modification is believed to increase the electrochemical activity of the carbon surface and increases the surface energy of the printed layers allowing for better adhesion between them and subsequently printed layers. Plasma treatment is also believed to improve the electrochemistry of the carbon surface making the reaction with the mediator more ideal as part of the electrochemical reaction during a measurement cycle.

Reagent layer 218 is disposed on a portion of conductive layer 250 and insulation layer 216, as illustrated in FIG. 2. In an embodiment, two overlapping reagent layers may be printed over a portion of conductive layer 250 and insulation layer 216.

Reagent layer 218 may include chemicals such as an enzyme and a mediator which selectively reacts with an analyte of interest and a buffer for maintaining a desired pH. For example, if glucose is to be determined in a blood sample, reagent layer 218 may include an enzyme and a mediator, along with other components necessary for functional operation. Enzymatic reagent layer 218 may include, for example, glucose oxidase, tri-sodium citrate, citric acid, polyvinyl alcohol, hydroxyl theyl cellulose, potassium ferricyanide, antifoam, cabosil, PVPVA, and water.

Exemplary enzymes suitable for use in the reagent layer include glucose oxidase, glucose dehydrogenase with a pyrroloquinoline quinone (PQQ) co-factor and glucose dehydrogenase with a flavin adenine dinucleotide (FAD) co-factor. An exemplary mediator suitable for use in the reagent layer includes ferricyanide, which in this case is in the oxidized form. The reagent layer may be configured to physically transform glucose into an enzymatic by-product and in the process generate an amount of reduced mediator (e.g., ferrocyanide) that is proportional to the glucose concentration value. Further details regarding reagent layers, and electrochemical-based analytical test strips in general, are in U.S. Pat. No. 6,241,862, the contents of which are hereby fully incorporated by reference into this application.

In one embodiment, the area of reagent layer 218 is sufficiently large to cover the entire area of reference electrode 210, first working electrode 212 and second working electrode 214. Reagent layer 218 includes a width and a length that is sufficiently large to at least account for the largest electrode area that may be used in test strip 200. The width of reagent layer 218 may be about 2 millimeters, which is more than double a width of rectangular aperture 217.

Adhesive layer 260 includes a first adhesive pad 262, a second adhesive pad 264 and a third adhesive pad 266 and may be disposed on test strip 200 after the deposition of reagent layer 218. Portions of adhesive layer 260 may be aligned to be immediately adjacent to, touch, or partially overlap with reagent layer 218. Adhesive layer 260 may include a water based acrylic copolymer pressure sensitive adhesive that is commercially available. Adhesive layer 260 is disposed on a portion of insulation layer 216, conductive layer 250, and substrate 205. Adhesive layer 260 binds hydrophilic layer 270 to test strip 200.

Hydrophilic layer 270 may include a distal hydrophilic portion 272 and proximal hydrophilic portion 274, as illustrated in FIG. 2. A gap 276 is included between distal hydrophilic portion 272 and proximal hydrophilic portion 274. Gap 276 serves as a side vent for air as blood fills sample-receiving chamber 292 (shown in FIG. 3). Hydrophilic layer 270 may be a polyester material having one hydrophilic surface such as an anti-fog coating, which is commercially available from 3M.

The final layer to be added to test strip 200 is top layer 280, as illustrated in FIGS. 2 and 3. Top layer 280 may include a clear portion 282 and opaque portion 284. Top layer 280 is disposed on and adhered to hydrophilic layer 270. Top layer 280 may be a polyester that has an adhesive coating on one side. It should be noted in FIG. 3 that a clear portion 282 may substantially overlaps distal hydrophilic portion 272, which allows a user to visually confirm that sample-receiving chamber 292 may be sufficiently filled. Opaque portion 238 helps the user observe a high degree of contrast between a colored fluid such as, for example, blood within sample-receiving chamber 292 and opaque portion 284.

The measurement of glucose by the exemplary strip can be based on the selective oxidation of glucose by the enzyme glucose oxidase (GO). The reactions that can occur in a glucose test strip are summarized below in Equations 1 and 2.

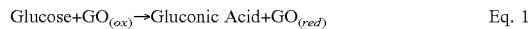

$$\text{Glucose} + \text{GO}_{(ox)} \rightarrow \text{Gluconic Acid} + \text{GO}_{(red)} \quad \text{Eq. 1}$$

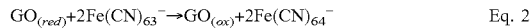

$$\text{GO}_{(red)} + 2\text{Fe(CN)}_6^{3-} \rightarrow \text{GO}_{(ox)} + 2\text{Fe(CN)}_6^{4-} \quad \text{Eq. 2}$$

As illustrated in Equation 1, glucose is oxidized to gluconic acid by the oxidized form of glucose oxidase ($\text{GO}_{(ox)}$). It should be noted that $\text{GO}_{(ox)}$ may also be referred to as an "oxidized enzyme." During the reaction in Equation 1, the oxidized enzyme $\text{GO}_{(ox)}$ is transformed to its reduced state, which is denoted as $\text{GO}_{(red)}$ (i.e., "reduced enzyme"). Next, the reduced enzyme $\text{GO}_{(red)}$ is re-oxidized or transformed back to $\text{GO}_{(ox)}$ by reaction with $\text{Fe(CN)}_6^{3-}$ (referred to as either the oxidized mediator or ferricyanide) as illustrated in Equation 2. During the re-generation of $\text{GO}_{(red)}$ back to its oxidized state $\text{GO}_{(ox)}$, $\text{Fe(CN)}_6^{3-}$ is reduced or transformed to $\text{Fe(CN)}_6^{4-}$ (referred to as either reduced mediator or ferrocyanide).

When the reactions set forth above are conducted with a test voltage applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, is referred to as a glucose current.

Figure 4:
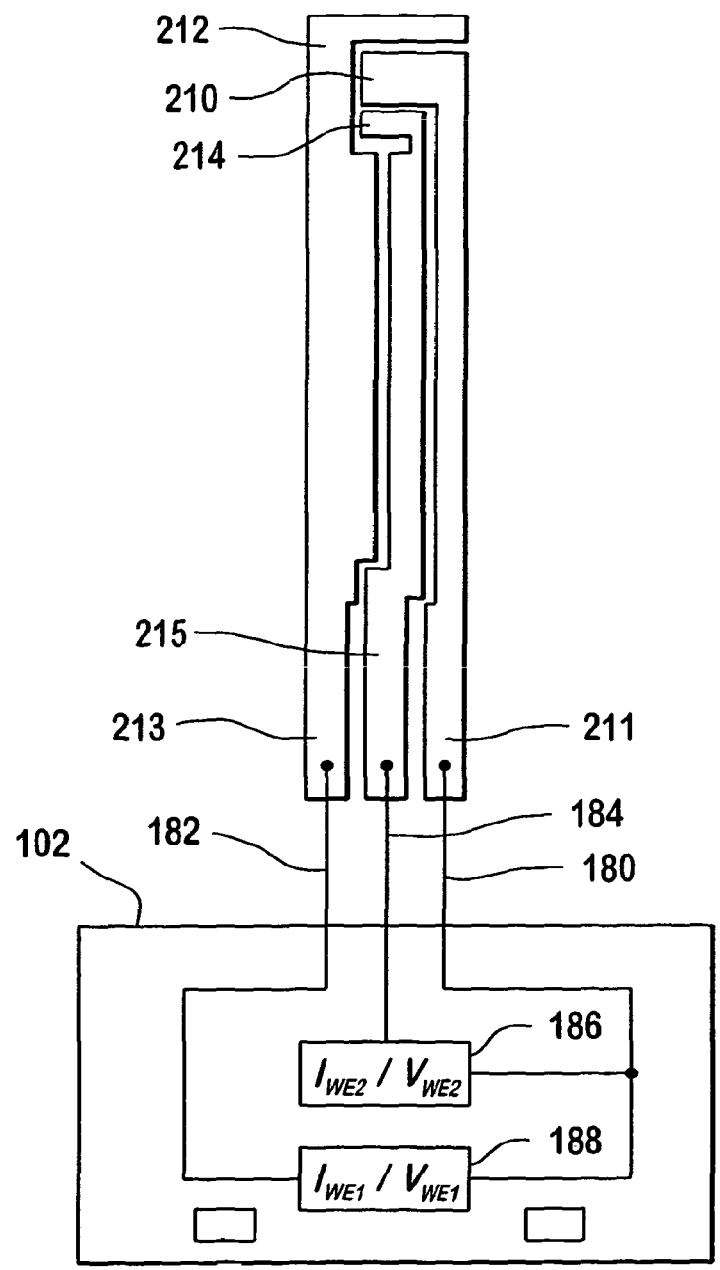
FIG. 4 illustrates an exemplary embodiment of a schematic of the functional components of the meter shown in FIG. 1A forming an electrical connection with the test strip of FIGS. 2 and 3.

FIG. 4 shows a simplified schematic of meter 102 interfacing with test strip 200. Meter 102 may include a reference connector 180, a first connector 182 and a second connector 184, which respectively form an electrical connection to reference contact 211, first contact 213 and second contact 215. The three aforementioned connectors are part of strip port 110. When performing a test, a first test voltage source 186 (from the circuit of FIG. 1B) may apply a test voltage $V_{WE2}$ between second working electrode 214 and reference electrode 210. As a result of test voltage $V_{WE2}$, meter 102 (via the microprocessor) may then measure a test current $I_{WE2}$ at second working electrode. In a similar manner, a second test voltage source 188 (from the circuit of FIG. 1B) applies a test voltage $V_{WE1}$ between first working electrode 212 and reference electrode 210. As a result of test voltage $V_{WE1}$, meter 102 may then measure a test current $I_{WE1}$. In an embodiment, test voltage $V_{WE2}$ and second test voltage $V_{WE1}$ may be about equal.

Figure 5:
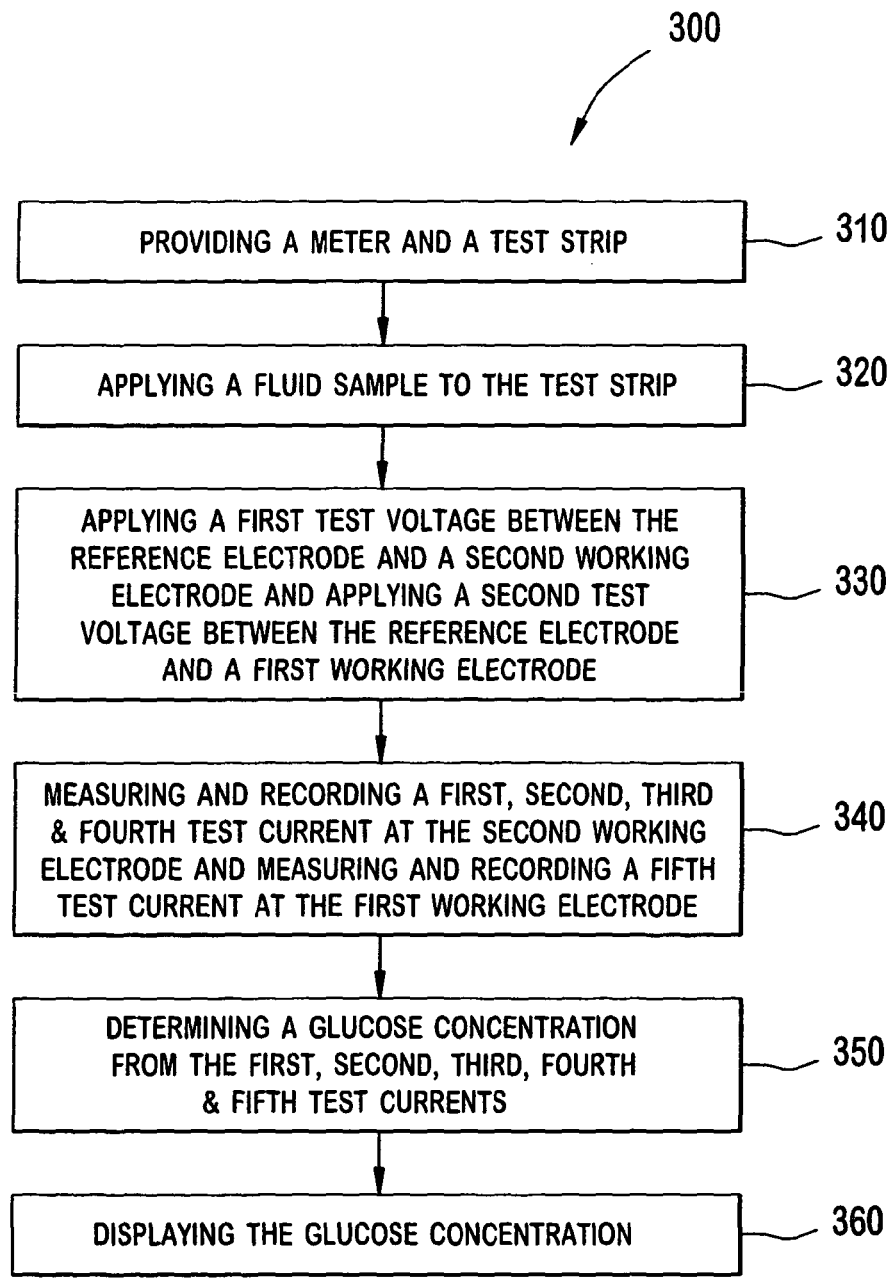
FIG. 5 illustrates an exemplary embodiment of a flow chart of a method of estimating a hematocrit-corrected glucose concentration using the system shown in FIG. 1A.

Referring to FIG. 5, a method 300 for determining a hematocrit-corrected analyte concentration (e.g., glucose) that uses the aforementioned meter 102 and test strip 200 embodiments will now be described.

In exemplary step 310, meter 102 and test strip 200 are provided. Meter 102 may include electronic circuitry that can be used to apply a first and second test voltage to the test strip and to measure current flowing through the second working electrode 214 and the first working electrode 212, respectively, as part of the transformation of $\text{GO}_{(red)}$ back to its oxidized state $\text{GO}_{(ox)}$ by the test strip electrochemical process illustrated in Equations 1 and 2. Meter 102 also may include a signal processor 162 with a set of instructions for the method of determining an analyte concentration in a fluid sample as disclosed herein.

Figure 6A:
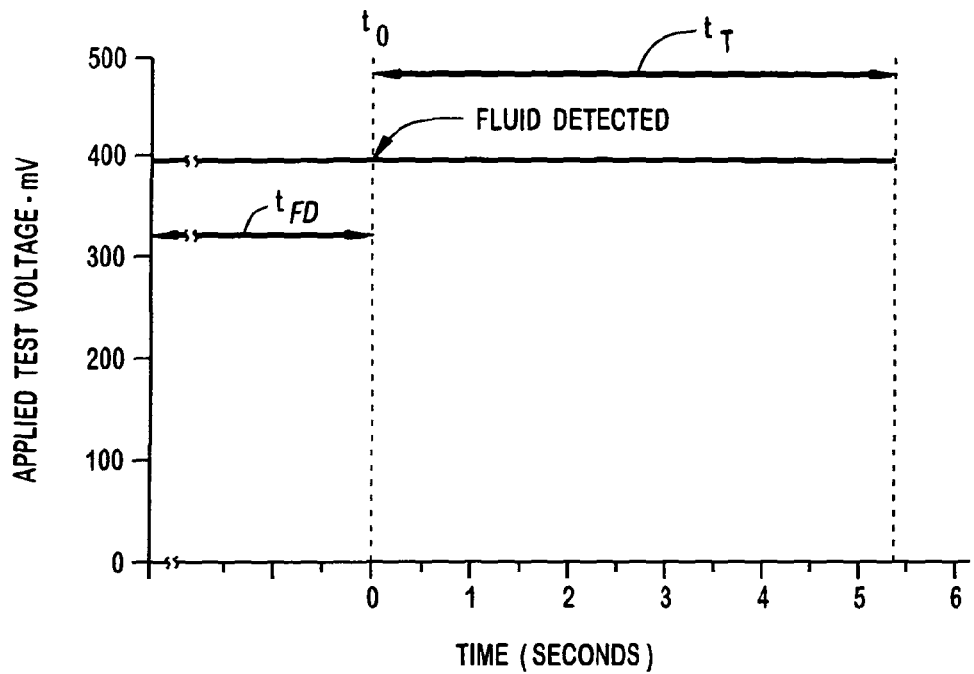
FIG. 6A illustrates an exemplary embodiment of a chart showing test voltages applied by the meter to the test strip.

FIG. 6A is an exemplary chart of a test voltage applied to test strip 200. Before a biological fluid sample is applied to test strip 200, test meter 102 is in a fluid detection mode in which a first test voltage of about 400 millivolts is applied between second working electrode 214 and reference electrode 210. A second test voltage of about 400 millivolts is preferably applied simultaneously between first working electrode 212 and reference electrode 210. Alternatively, the second test voltage may also be applied contemporaneously such that a time interval of the application of the first test voltage overlaps with a time interval in the application of the second test voltage. The test meter may be in a fluid detection mode during fluid detection time interval $t_{FD}$ prior to the detection of physiological fluid at time $t_0$. In the fluid detection mode, test meter 102 determines when a fluid is applied to test strip 200 in exemplary step 320 such that the fluid wets second working electrode 214 and reference electrode 210. Once test meter 102 recognizes that the physiological fluid has been applied because of, for example, a sufficient increase in the measured test current at second working electrode 214, test meter 102 assigns a zero second marker at time $t_0$ and starts the test time interval $t_T$. Upon the completion of the test time interval $t_T$, the test voltage is removed. For simplicity, FIG. 6A only shows the first test voltage applied to test strip 200.

Figure 6B:
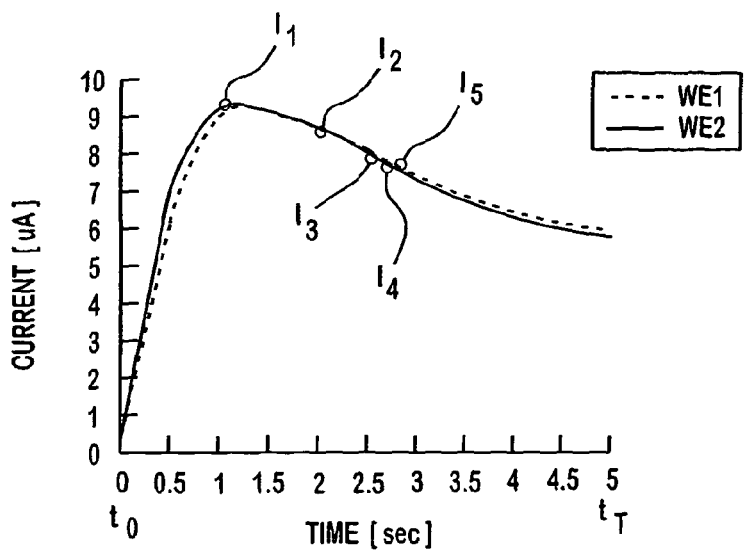
FIG. 6B illustrates an exemplary embodiment of a chart showing test currents generated when the test voltages of FIG. 6A are applied to the test strip.

FIG. 6B is an exemplary chart of current transients (i.e., the measured electrical current response in microamperes as a function of time) that are measured when the test voltages of FIG. 6A are applied to test strip 200. Test currents $I_i$ obtained from current transients are generally indicative of the analyte concentration in the sample. Referring to FIGS. 5 and 6A, in exemplary step 330, the first test voltage is applied between second working electrode 214 and reference electrode 210 and a second test voltage is applied between first working electrode 212 and reference electrode 210 at time $t_0$. In exemplary step 340, a first test current $I_1$, a second test current $I_2$, a third test current $I_3$ and a fourth test current $I_4$ are measured at times $t_2$, $t_3$, $t_4$ and $t_5$, respectively, at second working electrode 214. These currents $I_i$ where i=1, 2, 3, 4 . . . n are stored or recorded in the memory unit of the meter for analysis. In exemplary step 340, a fifth test current $I_5$ is also measured at time $t_6$ at first working electrode 212. The first and second test voltages applied to test strip 200 are generally from about +100 millivolts to about +600 millivolts. In one embodiment in which the electrodes include carbon ink and the mediator is ferricyanide, the test voltage is about +400 millivolts. Other mediator and electrode material combinations will require different test voltages. The duration of the test voltages is typically about 5 seconds. Typically, time $t_i$ is measured relative to time $t_0$. In practice, each test current $I_i$ is the average of a set of measurements obtained over a short interval, for example, five measurements obtained at 0.01 second intervals starting at $t_{i+1}$, where I ranges from 1 to at least 6.

Referring to FIG. 5 in exemplary step 350, a hematocrit-corrected glucose concentration may be determined with the following equation that utilizes current transient measured from the transformation of $GO_{(red)}$ back to its oxidized state $GO_{(ox)}$:

$$G = \frac{\left(\frac{a*I_5+b}{\left(\frac{c*\left(\frac{I_2-I_1}{d}\right)+e}{f*(I_2*I_1)+g}\right)*\left(\frac{h*\left(\frac{I_4-I_3}{k}\right)+p}{q*(I_4*I_3)+s}\right)}\right) - \text{intercept}}{\text{slope}} \quad \text{Eq. 3}$$

where:
G is the hematocrit-corrected glucose concentration;
$I_1$ is the first test current;
$I_2$ is the second test current;
$I_3$ is the third test current;
$I_4$ is the second test current;
$I_5$ is the third test current;
a, b, c, d, e, f, g, h, k, p, q and s are empirically derived constants;
intercept is an intercept value determined from a linear regression of a plot of $$\frac{a*I_5+b}{\left(\frac{c*\left(\frac{I_2-I_1}{d}\right)+e}{f*(I_2*I_1)+g}\right)*\left(\frac{h*\left(\frac{I_4-I_3}{k}\right)+p}{q*(I_4*I_3)+s}\right)}$$

versus a reference glucose concentration. In a preferred embodiment, intercept may be equal generally to about −2.86; and slope is a slope value determined from a linear regression of a plot of $$\frac{a*I_5+b}{\left(\frac{c*\left(\frac{I_2-I_1}{d}\right)+e}{f*(I_2*I_1)+g}\right)*\left(\frac{h*\left(\frac{I_4-I_3}{k}\right)+p}{q*(I_4*I_3)+s}\right)}$$

versus the reference glucose concentration. In a preferred embodiment, slope may be equal generally to about −0.000545.

In a preferred embodiment, first test current $I_1$ may be measured at about 1.98 seconds to about 2.26 seconds after time $t_0$, second test current $I_2$ may be measured at about 2.90 seconds to about 2.98 seconds after time $t_0$, third test current $I_3$ may be measured at about 3.01 seconds to about 3.09 seconds after time $t_0$, fourth test current may be measured at about 0.95 seconds to about 1.03 seconds after time $t_0$ and fifth test current may be measured at about 4.74 seconds to about 4.82 seconds after time $t_0$.

In preferred embodiment, a is from about 0.0158 to about 0.0162, b is from about 3.55 to about 3.59, c is from about 24.2 to about 24.6, d is from about 71.1 to about 71.5, e is from about 6.89 to about 6.93, f is from about 0.27 to about 0.31, g is from about 81.8 to about 82.2, h is from about 102 to about 104, k is from about −453 to about −455, p is from about −0.0686 to about −0.0690 and q is from about 30.2 to about 30.6.

In exemplary step 360, the hematocrit-corrected glucose concentration may then be annunciated on meter 102.

Example 1

Determination of Hematocrit-Corrected Glucose

A batch of test strips was tested with 10776 whole blood samples having three different glucose concentrations (i.e., 50 mg/dL, 150 mg/dL and 450 mg/dL) and hematocrit levels ranging from 29 to 56%. Test currents were measured at the second working electrode at 0.99, 2.22, 2.94 and 3.05 seconds and at the first working electrode at 4.78 seconds. The hematocrit-corrected glucose concentration was determined for each data point as described previously with method 300 (i.e., no reaction period prior to application of the test voltages).

An uncorrected glucose concentration was also determined for the same set of whole blood samples as above (i.e., 10776 whole blood samples) having three different glucose concentrations (i.e., 50 mg/dL, 150 mg/dL and 450 mg/dL) and hematocrit levels ranging from 29 to 56%. The same batch of test strips was used. A test current at 5 seconds (hereinafter called the "end current") was measured and recorded for each sample. The uncorrected glucose concentration was then determined from a calibration curve table stored in the meter. A calibration curve may be generated from the end current data by graphing end current as a function of known glucose concentration as measured on a reference instrument.

The bias, which is an estimate of the relative error in the glucose measurement, was next calculated for each glucose concentration determined with the three methods described in Examples 1 and 2 (i.e., endpoint current, method 300 and method 400). The bias for each glucose concentration was determined with equations of the form:

$$\text{Bias}_{abs} = G_{calculated} - \quad \text{Eq. 4}$$
$G_{reference}$ for $G_{reference}$ less than 75 mg/dL glucose and
with a bias target of about 15 mg/dL or about 20% and $$\text{Bias}_{\%} = \frac{G_{calculated} - G_{reference}}{G_{reference}} \text{ for } G_{reference} \text{ greater} \quad \text{Eq. 5}$$
than or equal to 75 mg/dL glucose and with
a bias target of about 15 mg/dL or about 20%;

where Bias$_{abs}$ is absolute bias,
Bias$_\%$ is percent bias,
G$_{calculated}$ is the glucose concentration determined by one of three methods described in Examples 1 and 2 and
G$_{reference}$ is the reference glucose concentration.

Note that the limits for G$_{reference}$ at which Equation 4 and Equation 5 apply vary according to the bias target. For example, if the bias target is 12 mg/dL or 15%, then Equation 4 is used for G$_{reference\ less}$ than 80 mg/dL glucose and Equation 5 is used for G$_{reference}$ greater than or equal to 80 mg/dL.

Figure 7:
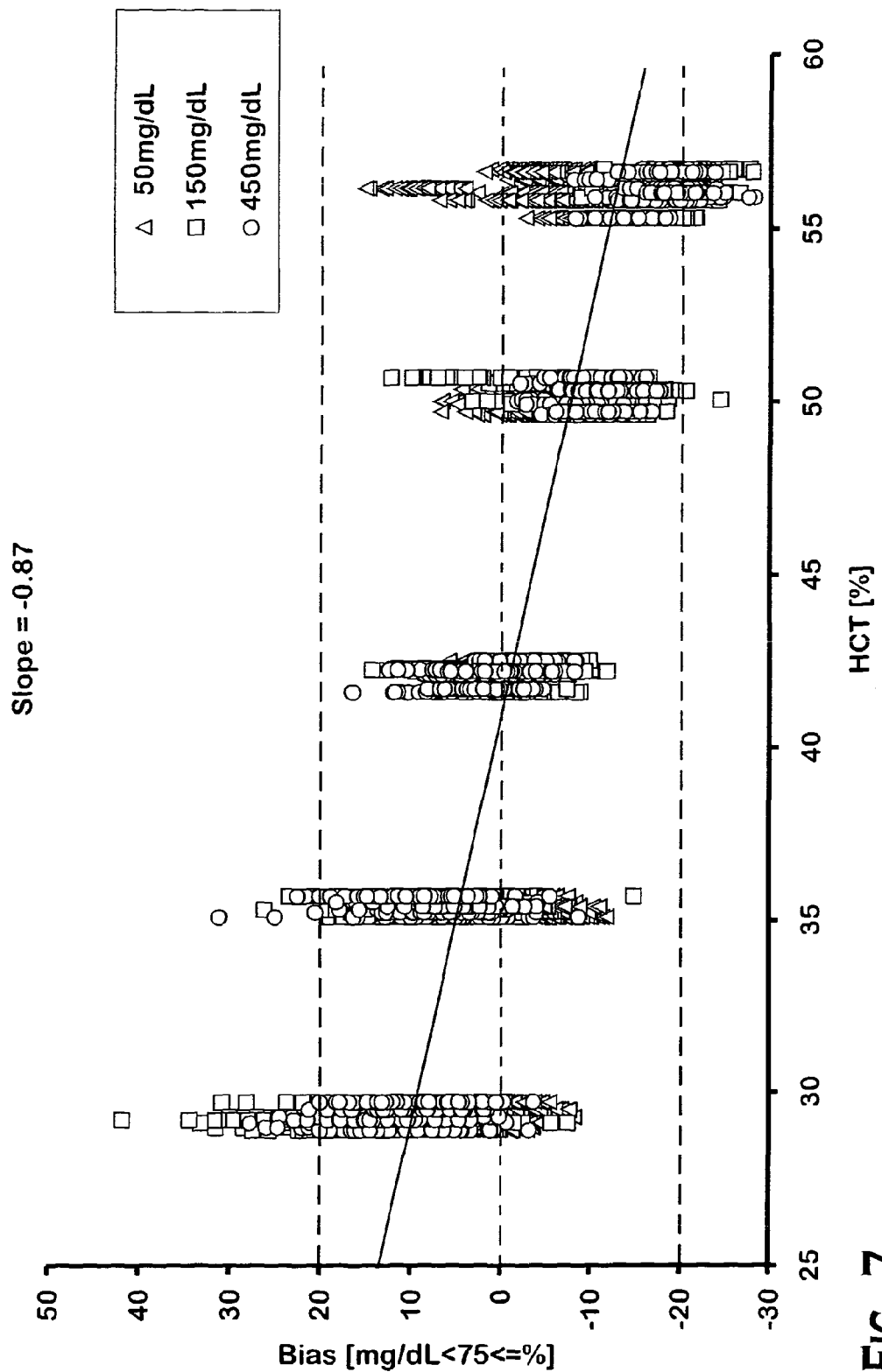
FIG. 7 illustrates a bias plot of test data obtained with an end current algorithm.
Figure 8:
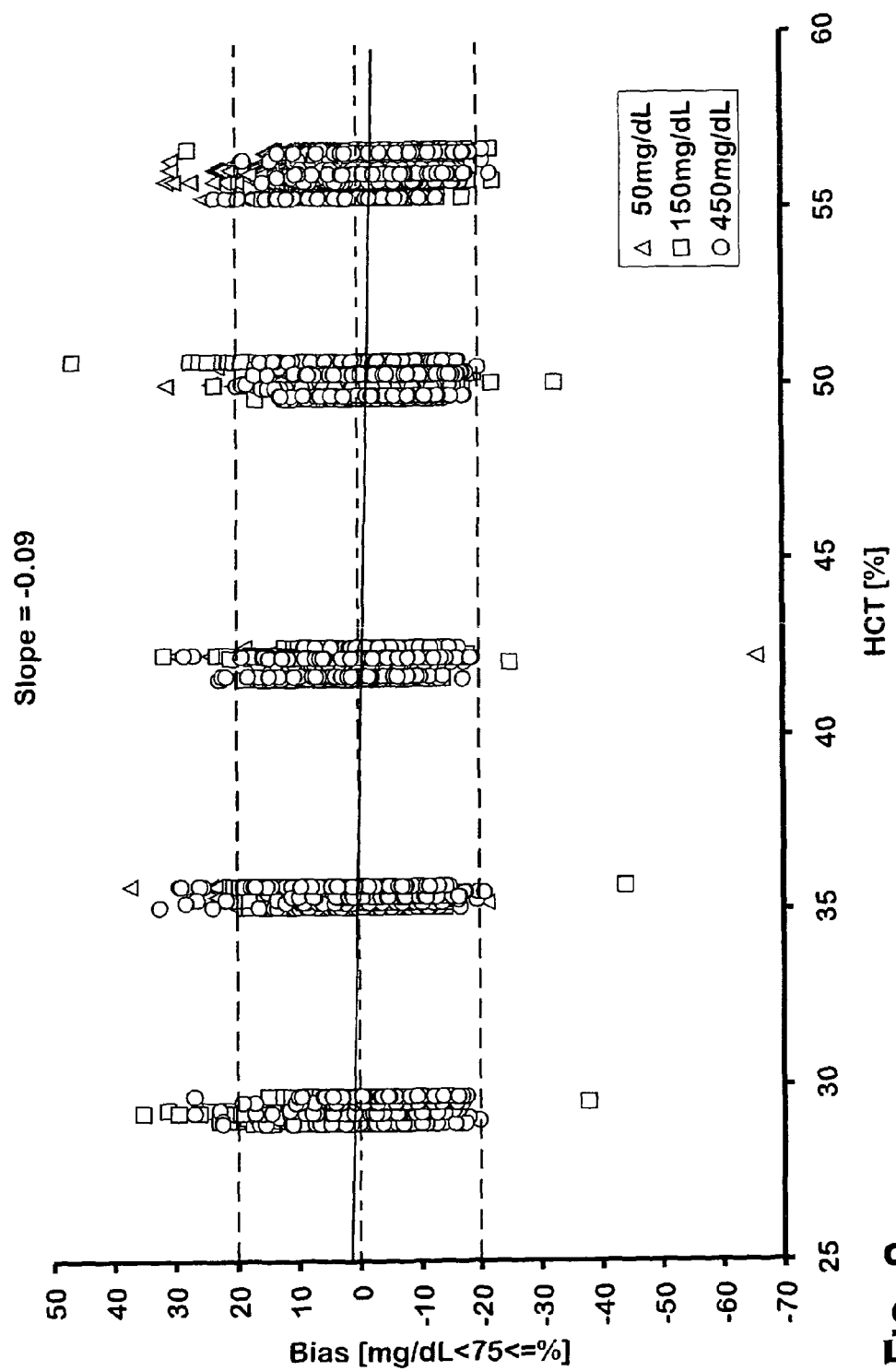
FIG. 8 illustrates a bias plot of test data obtained with an embodiment of the current invention.

FIGS. 7 and 8 illustrate bias plots of bias versus percent hematocrit. FIG. 7 illustrates the bias plot of data in which the end current was used to determine the glucose concentration. The end current measurement as applied in an experimental batch of strips which are believed to have hematocrit interference. The interference is believed to introduce a bias as an additional error source in the glucose concentration reading. This bias is apparently roughly zero at nominal hematocrit (42%). Towards lower hematocrit the bias introduced is roughly 1 mg/dL per every percent of hematocrit lower than nominal and −1 mg/dL per every percent of hematocrit higher than nominal. This error is believed to be large enough at the corners (at 30% & 55%) of this batch of strip to impact accuracy of the strip.

FIG. 8 illustrates the bias plot of data as determined by method 300. The preferred embodiment is believed to flatten the hematocrit response of the exemplary strip to a sufficient degree as shown below in Table 1. A previous algorithm was developed in an attempt to solve this problem, which also removed largely the haematocrit bias. Unfortunately, such prior approach suffered from large precision issue and did not work as a single-calibration code implementation. The preferred approach on the other hand works well in the exemplary strip that utilizes a single calibration code and does not increase standard deviation for any HCT/YSi splits.

The data from FIGS. 7 and 8 may also be presented as a percent falling within different ISO (International Standards Organization) bias criteria, as illustrated in Table 1 below.

TABLE 1

Summary of Bias Results

| ISO Bias Criteria Approx. (mg/dL or %) | Percent within Bias Criteria for Endpoint algorithm (Reference) | Percent within Bias Criteria for Method 300 |
|---|---|---|
| +/−15 mg/dL or 20% | 94.1 | 97.9 |
| +/−12 mg/dL or 15% | 81.8 | 94.5 |
| +/−10 mg/dL or 12% | 71.4 | 88.4 |

The data in Table 1 indicates an increase in the percentage of data when method 300 is used to correct the data for the hematocrit effect falling within each ISO bias criteria as compared to a referential method.

As noted earlier, a microprocessor can be programmed to generally carry out the steps of various processes described herein. The microprocessor can be part of a particular device, such as, for example, a glucose meter, an insulin pen, an insulin pump, a server, a mobile phone, personal computer, or mobile hand held device. Furthermore, the various methods described herein can be used to generate software codes using off-the-shelf software development tools such as, for example, Visual Studio 6.0, C or C++ (and its variants), Windows 2000 Server, and SQL Server 2000. The methods, however, may be transformed into other software languages depending on the requirements and the availability of new software languages for coding the methods. Additionally, the various methods described, once transformed into suitable software codes, may be embodied in any computer-readable storage medium that, when executed by a suitable microprocessor or computer, are operable to carry out the steps described in these methods along with any other necessary steps.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method for determining a glucose concentration measurable with a system having a test strip and a meter, the method comprising:
   applying a first test voltage between a reference electrode and a second working electrode coated with a reagent layer and applying a second test voltage between a reference electrode and a first working electrode coated with a reagent layer;
   measuring a first test current, a second test current, a third test current and a fourth test current at the second working electrode in which blood containing glucose is applied to the test strip to cause a transformation of the glucose in the blood from one form of glucose into another form of glucose and generate a current by an electrochemical re-oxidation of a reduced mediator applied to the test strip;
   measuring a fifth test current at the first working electrode;
   determining the glucose concentration from the first, second, third, fourth and fifth test currents with an equation of the form:

$$G = \frac{\left(\dfrac{a*I_5 + b}{\left(\dfrac{c*\left(\dfrac{I_2 - I_1}{d}\right) + e}{f*(I_2*I_1) + g}\right) * \left(\dfrac{h*\left(\dfrac{I_4 - I_3}{k}\right) + p}{q*(I_4*I_3) + s}\right)}\right) - \text{intercept}}{\text{slope}}$$

where:
G comprises the glucose concentration;
$I_1$ comprises the first test current;
$I_2$ comprises the second test current;
$I_3$ comprises the third test current;
$I_4$ comprises the fourth test current;
$I_5$ comprises the fifth test current;
a, b, c, d, e, f, g, h, k, p, q and s each comprises empirically derived constants;
intercept comprises an intercept value determined from a linear regression of a plot of $$\frac{a*I_5+b}{\left(\frac{c*\left(\frac{I_2-I_1}{d}\right)+e}{f*(I_2*I_1)+g}\right)*\left(\frac{h*\left(\frac{I_4-I_3}{k}\right)+p}{q*(I_4*I_3)+s}\right)}$$

versus a reference glucose concentration; and slope comprises a slope value determined from a linear regression of a plot of $$\frac{a*I_5+b}{\left(\frac{c*\left(\frac{I_2-I_1}{d}\right)+e}{f*(I_2*I_1)+g}\right)*\left(\frac{h*\left(\frac{I_4-I_3}{k}\right)+p}{q*(I_4*I_3)+s}\right)}$$

versus the reference glucose concentration.

2. The method of claim 1, in which the reference electrode, the first electrode and the second electrodes are disposed on a single plane.

3. The method of claim 1, in which the first test current is measured from about 2.18 to about 2.26 seconds after initiation of the measuring.

4. The method of claim 1, in which the second current is measured from about 2.90 to about 2.98 seconds after initiation of the measuring.

5. The method of claim 1, in which the third current is measured from about 3.01 to about 3.09 seconds after initiation of the measuring.

6. The method of claim 1, in which the fourth current is measured from about 0.95 to about 1.03 seconds after initiation of the measuring.

7. The method of claim 1, in which the fifth current is measured from about 4.74 to about 4.82 seconds after initiation of the measuring.

8. The method of claim 1, in which a comprises from about 0.0158 to about 0.0162, b comprises from about 3.55 to about 3.59, c comprises from about 24.2 to about 24.6, d comprises from about 71.1 to about 71.5, e comprises from about 6.89 to about 6.93, f comprises from about 0.27 to about 0.31, g comprises from about 81.8 to about 82.2, h comprises from about 102 to about 104, k comprises from about −453 to about −455, p comprises from about −0.0686 to about −0.0690 and q comprises from about 30.2 to about 30.6.

9. The method of claim 1, in which the slope comprises a value of about minus 0.000545 and the intercept comprises a value of about minus 2.86.

10. A method for determining a hematocrit-corrected test current measurable with a system having a test strip and a meter, the method comprising:

applying a first test voltage between a reference electrode and a second working electrode coated with a reagent layer and applying a second test voltage between a reference electrode and a first working electrode coated with a reagent layer;

measuring a first test current, a second test current, a third test current and a fourth test current at the second working electrode in which blood containing glucose is applied to the test strip to cause a transformation of the glucose in the blood from one form of glucose into another form of glucose and generate a current by an electrochemical re-oxidation of a reduced mediator applied to the test strip;

measuring a fifth test current at the first working electrode; and determining the hematocrit-corrected test current by determining a ratio of a third corrected current to a first corrected current multiplied by a second corrected current.

11. The method of claim 10, in which the third corrected current comprises a value determined by an equation of the form:

$ic3 = a*I_5 + b$ where:

ic3 comprises the third corrected current;

$I_5$ comprises the fifth test current; and a and b each comprises an empirically derived constant.

12. The method of claim 10, in which the first corrected current comprises a value determined by an equation of the form:

$$ic1 = \frac{c*\left(\frac{I_2-I_1}{d}\right)+e}{f*(I_2*I_1)+g}$$

where:

ic1 comprises the third corrected current;

$I_1$ comprises the first test current;

$I_2$ comprises the second test current; and c, d, e, f and g comprise empirically derived constants.

13. The method of claim 10, in which the second corrected current comprises a value determined by an equation of the form:

$$ic2 = \frac{h*\left(\frac{I_4-I_3}{k}\right)+p}{q*(I_4*I_3)+s}$$

where:

ic2 comprises the third corrected current;

$I_3$ comprises the third test current;

$I_4$ comprises the fourth test current; and h, k, p, q and s comprise empirically derived constants.

14. The method of claim 10, in which the first test current comprises a current measured from about 2.18 to about 2.26 seconds after initiation of the measuring; the second current comprises a current measured from about 2.90 to about 2.98 seconds after initiation of the measuring; the third current comprises a current measured from about 3.01 to about 3.09 seconds after initiation of the measuring; the fourth current comprises a current measured from about 0.95 to about 1.03 seconds after initiation of the measuring; and the fifth current comprises a current measured from about 4.74 to about 4.82 seconds after initiation of the measuring.

* * * * *